United States Patent [19]

Bechtel

[11] Patent Number: 4,991,446
[45] Date of Patent: Feb. 12, 1991

[54] FORCE MEASUREMENT WITH COMPENSATION OF ERRORS CAUSED BY ACCELERATIONS OF MEASURING APPARATUS

[75] Inventor: Friend K. Bechtel, Moscow, Id.

[73] Assignee: Metriguard, Inc., Pullman, Wash.

[21] Appl. No.: 417,898

[22] Filed: Oct. 5, 1989

[51] Int. Cl.⁵ .............................................. G01N 3/20
[52] U.S. Cl. ....................................... 73/849; 73/852; 73/DIG. 10
[58] Field of Search ............ 73/812, 849, 852, 862.67, 73/DIG. 10

[56] References Cited

U.S. PATENT DOCUMENTS

| | | | |
|---|---|---|---|
| 2,767,974 | 10/1956 | Ballard et al. | 73/DIG. 10 |
| 3,194,063 | 7/1965 | McKean | 73/100 |
| 3,196,672 | 7/1965 | Keller | 73/100 |
| 3,201,983 | 8/1965 | Hebert et al. | 73/862.67 |
| 4,531,600 | 7/1985 | Langlais et al. | 73/862.67 |

OTHER PUBLICATIONS

Metriguard, Inc., brochure, "CLT-Continuous Lumber Tester".
Unpublished description of "Prior Art", improvement to CLT equipment, titled Inertial Compensator for CLT as Developed and Installed in 1978, by Metriguard, Inc., Pullman, Wash., Aug. 1989.

Primary Examiner—Robert Raevis
Attorney, Agent, or Firm—Wells, St. John & Roberts

[57] ABSTRACT

A method and apparatus for compensating for errors in the measurement of force applied to a load beam interposed between two compliant supports and a load point involves placement of an accelerometer at a selected location on the load beam. Signals produced by the accelerometer are added to a signal produced by a transducer at one of the compliant supports to obtain a composite signal which is compensated for accelerations of the load beam.

13 Claims, 5 Drawing Sheets

FIG 5

FORCE MEASUREMENT WITH COMPENSATION OF ERRORS CAUSED BY ACCELERATIONS OF MEASURING APPARATUS

TECHNICAL FIELD

This disclosure relates to the compensation for force measurement errors caused by accelerations of an apparatus between a load point and a force measuring transducer. Equipment of this type is used to apply and/or measure forces to lumber or other materials for the purpose of sorting the material into grades or controlling material manufacturing processes.

BACKGROUND OF THE INVENTION

In the sorting of lumber according to its bending stiffness, the process most commonly used in high speed production facilities in North America bends the lumber in a machine with a series of rollers as the lumber passes longitudinally through the machine. Background information on such testing processes and equipment can be found in U.S. Pat. Nos. 3,194,063 (McKean) and 3,196,672 (Keller), which are hereby incorporated into this disclosure by reference. A commercial implementation of Keller's patent is entitled "CLT—CONTINUOUS LUMBER TESTER", produced and sold by Metriguard, Inc., Pullman, Wa. For brevity, this described machine will be identified as the "CLT".

To achieve bending stiffness measurements, the CLT utilizes two bending sections; in the first, the lumber is bent downward by a fixed amount, and in the second, the lumber is bent upward by a fixed amount. The force measurements from the two bending sections are averaged to give a result that is independent of deviations from straightness in the lumber. In each bending section, the lumber bending deflection is maintained substantially constant. Lumber sorted according to its bending stiffness together with some visual restrictions and offline quality control procedures can be marketed as Machine Stress Rated (MSR) lumber.

In the CLT, bending deflection of the lumber is caused by a load beam assembly with a pivot on one end and a force measuring transducer on the other. At a point along the load beam assembly, a load point applies the force required to bend the lumber by a prescribed amount. Or, one can say that the lumber applies a force to the load beam assembly at the load point. In the CLT example, the load point consists of a line contact that a load roller makes with the lumber, where the load roller is mounted by bearings to the load beam assembly. At high speeds, constant lumber deflection and fixed position of the load beam assembly are important because that substantially reduces errors at the force measuring transducer that are caused by accelerations of the load beam assembly.

In practice, even though care is taken to reduce the movements, and hence accelerations of the load beam assembly, some extraneous accelerations remain due to various forces that result from the lumber moving through the machine and from external sources, such as vibrating machinery in the area. These accelerations are most pronounced in the second of the CLT's two bending sections. In the second bending section, the load beam assembly is mounted to a bridge frame that is itself suspended from lower clamp roller bearing points that move up and down slightly as lumber enters and exits the bending section. The movement is required to allow the lower clamp rollers to properly clamp and reference the lumber upwardly against the upper clamp rollers at the ends of the bending span. Proper setup and careful control of lumber thickness minimize the motion required for clamping, but even after all care is exerted, some accelerations remain. Because of the inertia of the load beam assembly, these accelerations show up in the measurement as noise superimposed on the desired output signal and hence they reduce the accuracy and resolution with which bending stiffness measurements can be made.

In 1978, Metriguard Inc. introduced an "inertial compensation" system which uses an accelerometer mounted at the base of the force measuring transducer in the second bending section to measure accelerations at the base of the force measuring transducer in directions along its axis and electronically cancel the acceleration-induced noise. This system improves the performance of the force measurement system but does not satisfactorily remove the noise over the conditions of vibration and shock inputs encountered in high speed lumber production facilities. The reason is that the load beam assembly is mounted and referenced to the CLT machine frame at two points and hence can have two independent components of mechanical excitation which are not completely resolved and corrected by measurements from the one accelerometer as presently configured.

It is the objective of this disclosure to describe a linear model of the load beam assembly and to define a selected location for a single compensating accelerometer whose signal can be used to satisfactorily compensate for the effects of acceleration inputs at both reference points where the load beam assembly is mounted. It will be seen that this compensation performs at all frequencies for which the model is valid.

The model consists of a rigid beam having a load point. The beam is supported by two compliant supports at two reference points along it. Mechanical inputs to the rigid beam are through the load point and through the compliant supports. Using superposition principles allows removing the input at the load point to analyze the effects of acceleration inputs at the compliant supports. It happens that a selected location on the beam can be determined such that a signal proportional to the acceleration at just this one point can be used to compensate for acceleration inputs at both compliant supports.

The rigid beam and the two compliant supports form a mechanical system that is excited by acceleration inputs at the compliant supports. For the analysis and computations, a reference direction is defined and only those components of force applied at the load point, force measured at the force transducer, and acceleration inputs that are aligned with the reference direction are considered. Mechanical linkages and/or gearing could be used to avoid this alignment, but here the idea is presented in simplest terms, and the preferred embodiment is described in these terms. In the CLT which provides the framework for the preferred embodiment, the reference direction is vertical.

Further relating the model to the CLT, the two compliant supports for referencing the load beam assembly to the CLT frame are comprised of a series combination of a force transducer and some compliance at one end of the load beam assembly, and a parallel combined effect of two coaxial stub shafts that form a pivot support at the other end of the load beam assembly. The stub shafts and their mounting to the CLT frame are not perfectly rigid, and thus they are best modeled as a compliant support. It will be clear that the first compliant support, being the series combination of the force transducer and load beam end, has force proportional to the compression of the first compliant support and that this force is also proportional to the component of compression for the force transducer alone.

The four state variables used in the analysis of the model are translational velocity of the rigid beam in the reference direction, rotational velocity of the beam about an axis perpendicular to a plane containing both the longitudinal axis of the beam and the reference direction, and compressions in the reference direction of both compliant supports, treating them as springs. Accelerations in the reference direction at the two compliant supports are treated as two input variables. One output variable is taken as the compression at the first compliant support, and a second output variable is taken as the acceleration in the reference direction of a selected location on the rigid beam. Using this model, it can be shown that these two output variables are identical, except for a known constant, over all combinations of the acceleration inputs, provided that the selected location of the output acceleration is chosen according to the present disclosure.

An electrical signal derived in the existing CLT design is proportional to the compression of the force transducer and is thus proportional to the force at the first compliant support. A desired component of this signal, because of the geometry of the load beam assembly, is proportional to the force in the reference direction applied by the lumber to the load roller; but a noise component caused by extraneous acceleration inputs at the compliant supports is also evident. It will be clear from this disclosure that a measure of acceleration in the reference direction at the selected location on the load beam assembly can be used to derive an electrical signal which, when combined with the electrical signal derived from the force transducer, will cause the acceleration-induced noise to be cancelled.

In the CLT at present, the acceleration induced noise is reduced partially by the inertial compensation technique introduced by Metriguard, Inc. in 1978 and further by electronic low-pass filtering of the signal. The filtering reduces the signal bandwidth and acts to attenuate frequency components of the signal including the noise above a cutoff frequency. If the acceleration induced noise component of the force transducer signal consists primarily of frequencies above the range of load point force signal frequencies of interest, then this is a satisfactory approach. In fact, until 1978, no compensation for the effects of these acceleration inputs was used. But, as accuracy and speed requirements have increased, it has become necessary to improve the measurement.

The inertial compensation introduced in 1978 caused a significant improvement, and as a result the system was retrofitted to most of the existing CLT machines and has become standard on all new ones. Since 1978, even higher machine speeds have become common, and the accuracy requirements have become more stringent. The high speeds require the ruggedness and hence massiveness of the present load beam assembly in order to survive; although it is recognized that reductions in mass would increase the frequencies of the acceleration induced noise component of the force transducer signal and hence make the noise more easily removable by low-pass filtering methods. Reducing the signal bandwidth by reducing the cutoff frequency of the low-pass filter would reduce the noise, but this would also reduce the spatial resolution of the force measurement along the lumber. From the correspondence between time and distance along the lumber as the lumber moves through the machine, it is clear that spatial resolution of the force measurement decreases as the machine speed increases, and to gain back this spatial resolution, it is necessary to increase the signal bandwidth. A summary of conflicting requirements is:

Reduce mass of load beam assembly to increase frequency content of acceleration induced noise.

Increase mass of load beam assembly to improve the ruggedness and durability of the machine at high production speeds.

Reduce cutoff frequency of electronic low-pass filter to remove more of the acceleration induced noise.

Increase cutoff frequency of electronic low-pass filter to improve the spatial resolution of the force measurement along the length of the lumber.

Decrease machine speed to improve the spatial resolution of the force measurement along the length of the lumber and reduce the magnitude of the acceleration excitation inputs.

Increase machine speed to reduce production costs and improve profitability.

The above requirements have led to engineering tradeoffs that are probably close to being optimum for the present system. But one fact is inescapable; speeds are increasing, and further improvements are necessary. The inertial compensation system of 1978 helped the situation by removing some of the acceleration induced noise; however, that system measures the acceleration at one point on the CLT bridge frame, and that does not compensate for enough of the induced noise.

The present disclosure shows that an optimum location exists at a selected location on the load beam assembly, such that measuring acceleration at the selected location makes possible significant further improvement in the reduction of acceleration induced noise. As a result, the cutoff frequency of the low-pass filter and hence signal bandwidth can be increased which leads directly to improved spatial resolution of the force measurement along the length of the lumber. This resolution improvement comes without the tradeoff penalties associated with the other means of increasing bandwidth.

The description is directed toward the understanding of a specific application in lumber testing. It is clear that the same solution to noise induced from accelerations is applicable in other force measurement situations where a similar load beam assembly model is valid.

BRIEF DESCRIPTION OF DRAWINGS

The preferred embodiment of the invention is illustrated in the accompanying drawings, in which.

DETAILED DESCRIPTION OF THE PREFERRED EMBODIMENT

The following disclosure of the invention is submitted in compliance with the constitutional purpose of the Patent Laws "to promote the progress of science and useful arts" (Article 1Section 8).

Figure 1:
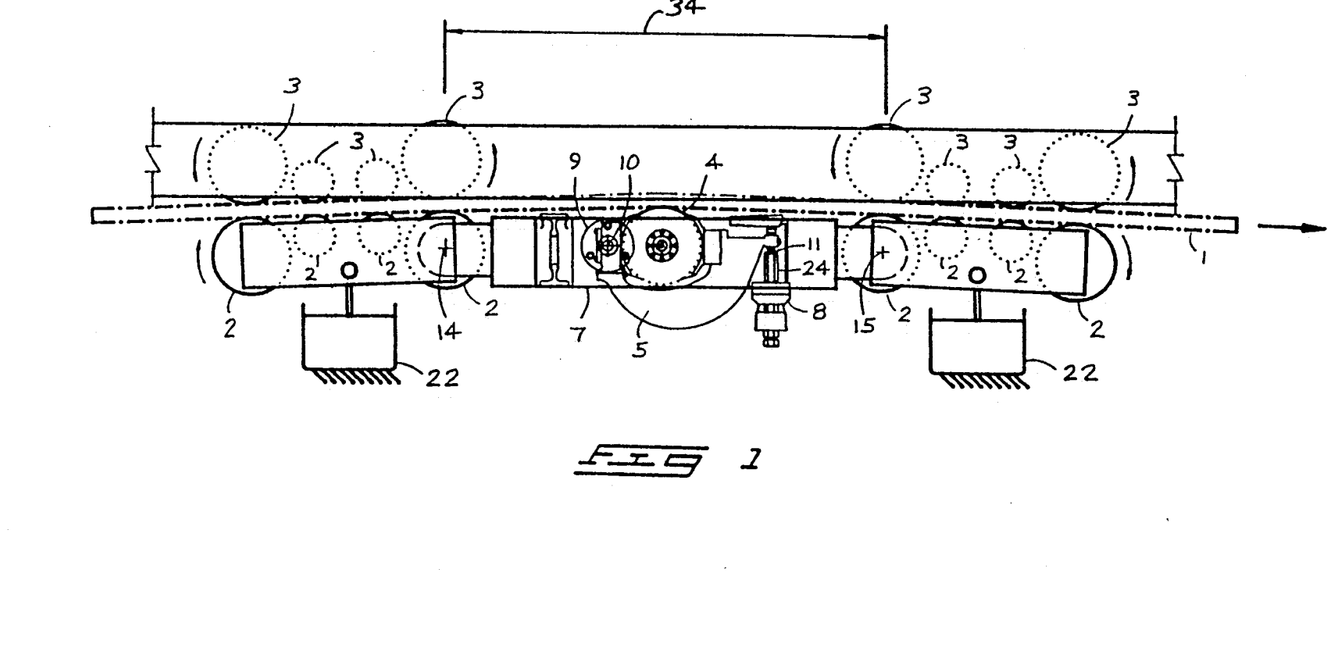
FIG. 1 is an elevation view illustrating the second bending section of a production-line machine, the CLT.

The apparatus used with the present system is shown in FIG. 1. When a piece of lumber 1 enters the space between the clamp rollers 2 and 3, it forces the lower rollers 2 to move downward slightly against air pressure in cylinders 22, from an upward stopped position. The lower clamp rollers 2 squeeze (clamp) the lumber against the upper clamp rollers 3, thereby defining the vertical position of the lumber at each end of a test span 34. The load roller 4 is part of a load beam assembly 5 and is attached to the load beam assembly by bearings. The load beam assembly is itself referenced and supported on a bridge frame 7 at a first reference point 11 by a force transducer 8 and interface bushing 24 and at a second reference point 10 by bearings 9. The supports at these load beam assembly reference points are best modeled as simple supports, as opposed to fixed supports.

Figure 2:
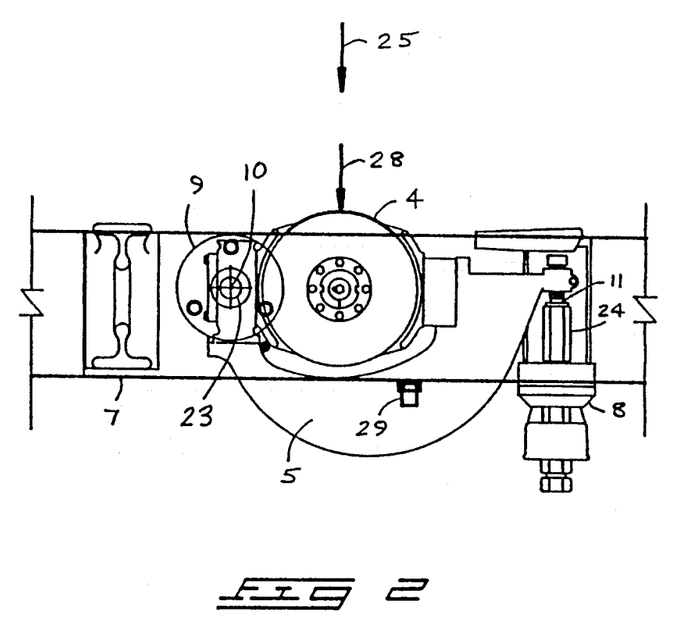
FIG. 2 is an elevation view of a force transducer and a load beam assembly, along with a section of the CLT bridge frame.
Figure 3:
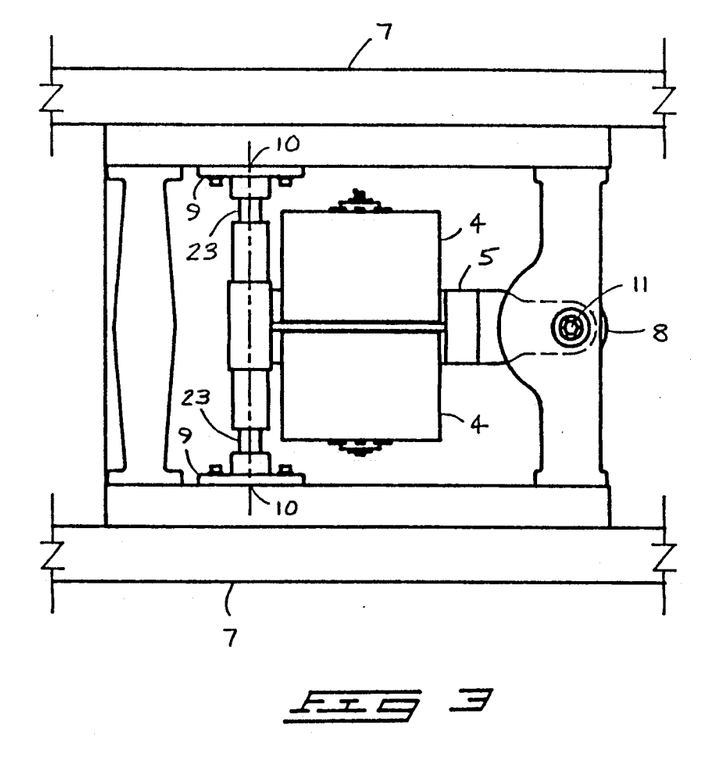
FIG. 3 is a plan view of the components illustrated in FIG. 2.

FIGS. 2 and 3 illustrate elevation and plan views respectively of the force transducer 8, load beam assembly 5, and load roller 4. Also shown are the load beam assembly reference points 10 and 11. These parts as described exist in commercial operating equipment, the CLT, for production of MSR lumber. Note that, except for input to the load point through the load roller, all mechanical inputs to the load beam assembly are through the two reference points 10 and 11; the second reference point 10 being at the simple support provided by the two bearings 9 at one end of the load beam assembly, and the first reference point 11 being at the simple support of the force transducer reference point at the other end.

Figure 4:
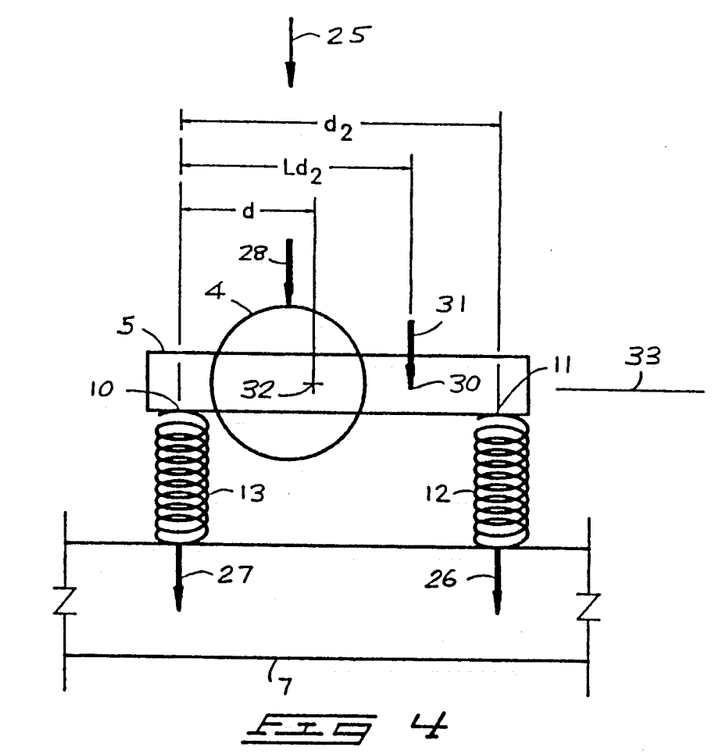
FIG. 4 illustrates a mechanical model of the system in FIG. 2.

FIG. 4 is a model of the pertinent components of FIGS. 2 and 3. The springs 12 and 13 represent compliance of the supports at the two reference points 10 and 11 of the load beam assembly 5.

Compliance of the support at second reference point 10 of the beam is caused by flexure of the load beam assembly attachment via stub shafts 23 to bearings 9 at that point. It is to be understood that for the preferred embodiment using commercially available equipment, there are two support points at second reference point 10 of the load beam assembly. These two supports are displaced laterally from one another on a common axis, but they are modeled as one support because they are located along the load beam assembly at a single location in the longitudinal direction.

Compliance of the support at first reference point 11 of the load beam assembly is caused by flexure in the force transducer and in the part of the load beam assembly making contact with the force transducer. A first signal, the electrical signal derived from the force transducer, is proportional to the compression of the force transducer and hence of the force at that point. This force via the mechanical leverage arrangement of the load beam assembly and the supports at reference points 10 and 11 is intended to be proportional to the force 28 applied by the lumber to the load point in a reference direction 25.

The bridge frame 7 shown in FIG. 1 is suspended from the axes 14 and 15 of the lower clamp rollers 2 nearest the ends of the test span. When lumber enters between the upper and lower clamp rollers, thereby causing the lower clamp rollers to move downward, the bridge frame accelerates downward first at 14 and then at 15. As the lumber exits, the rollers move back up. This motion can be resolved into acceleration inputs 26 and 27 at the compliant supports for the load beam assembly, the compliant supports being modeled by the springs 12 and 13 shown in FIG. 4. These accelerations and the inertia of the load beam assembly cause the springs to change in length and hence cause a change in the spring forces.

The system modeled by the springs and the load beam assembly is mechanically excited by these acceleration inputs. But, the force transducer is in series with, and is in fact part of, the spring 12. Consequently, the first signal which is proportional to the compression of spring 12, contains components caused by the acceleration inputs 26 and 27 acting through the springs 12 and 13 against the inertia of the load beam assembly. This noise in the first signal is due to the acceleration inputs 26 and 27 and to the inertia of the load beam assembly and acts to reduce the measurement accuracy of a desired signal, the desired signal being proportional to force 28 applied by the lumber to the load roller.

This disclosure shows that the acceleration 31 in the reference direction of the load beam assembly at a selected position 30 along the beam is directly proportional to the acceleration induced noise components of the first signal for any combination of acceleration inputs 26 and 27 over the entire frequency range for which the model of FIG. 4 is adequate. Then, a straightforward addition of the first signal and a second signal, the second signal being proportional to the acceleration 31 at the selected position, will cancel the noise components and leave a composite signal that is proportional to force applied to the load point in the reference direction.

Referring to FIG. 4, the selected location along the beam to measure the acceleration in the reference direction is specified by the fraction L of the distance $d_2$ between the reference points 10 and 11. The fraction L can be stated in terms of the following system parameters.

$K_1$ = spring constant (reciprocal compliance) of spring 12.

$K_2$ = spring constant (reciprocal compliance) of spring 13.

M = mass of load beam assembly.

d = distance from a line parallel to the reference direction 25 and passing through the second reference point 10, to a line parallel to the reference direction and passing through the center 32 of mass M.

$d_2$ = distance between lines parallel to the reference direction and passing through the first and second reference points 11 and 10.

$h = (d_2 - d)/d$ $z_1$ = compression of spring 12.

$T_1 = K_1/M$ $T_2 = K_2/M$

J = polar mass moment of parts comprising mass M about an axis through the center 32 of mass and perpendicular to the plane defined by the direction 33 along the load beam assembly and the reference direction 25.

$a_1$ = acceleration input 26 to the spring 12 in the reference direction 25.

$a_2$ = acceleration input 27 to the spring 13 in the reference direction 25.

a = acceleration in the reference direction 25 of the load beam assembly at the selected location.

R = Md²/J

The selected location for acceleration measurement is given by $Ld_2$, the distance $Ld_2$ being measured toward reference point 11 from a line in the reference direction through reference point 10. This specifies the selected location in a direction perpendicular to the reference direction and along the length of the load beam assembly. The specification of the selected location in a direction parallel to the reference direction is not critical, but practical considerations for the preferred embodiment have led to its approximate location as shown by accelerometer 29 in FIG. 2. This disclosure specifies that the fraction L is given by:

$$L = (1+R)/(R(1+h)) \quad (1)$$

If the acceleration "a" is measured at the selected location, then transfer functions relating the Laplace Transforms $A_1(s)$ and $A_2(s)$ of the input variables, consisting of accelerations $a_1$ and $a_2$, to the Laplace Transforms $Z_1(s)$ and $A(S)$ of the measured output variables, consisting of spring compression $z_1$ and acceleration "a", can be derived by known mathematical methods to state that:

$$Z_1(s) = -[(s^2 + T_2(1+R))/D]A_1(s) - [T_2(hR-1)/D]A_2(s) \quad (2)$$

$$A(s)/(T_1(1+h)) = [(s^2 + T_2(1+R))/D]A_1(s) + [T_2(hR-1)/D]A_2(s) \quad (3)$$

where s is the independent complex variable for the Laplace Transform and $$D = s^4 + s^2[T_2(1+R) + T_1(1+Rh^2)] + T_1T_2R(1+h)^2 \quad (4)$$

Comparison of Equation (3) with Equation (2) shows that except for the constant $C = -T_1(1+h) = -(K_1d_2)/(Md)$, $A(s)$ is identical to $Z_1(s)$ for all values of the complex variable s and for all input combinations of $A_1(s)$ and $A_2(s)$. This is a result of defining the output variable "a" as acceleration at the selected location 30 per equation (1). In other locations for measured acceleration "a", the acceleration and force transducer signals do not have this special relationship to one another.

It can be seen that the model of FIG. 4 and the results stated in Equations (2) and (3) do not include damping, and it is known that damping exists. However, it has been determined experimentally, that by following the teachings of this disclosure as though damping did not exist and then searching about the computed value L for the value giving best agreement between the first and second signals, a best location does exist near the computed value. Further, such an experimental search is often desirable because of uncertainties in knowledge of $K_1$, $K_2$, M, J and d. Best agreement can be defined in different ways. One practical method is to excite the system with acceleration inputs at the compliant supports and then minimize average power in the composite signal formed by adding the first and second signals. Minimization would occur over the parameter L defining the acceleration measurement location 30 and the value of proportionality constant C relating acceleration to the second signal.

Although the CLT as a framework for the preferred embodiment requires a vertical reference direction, it is clear that the entire apparatus and frame of reference could be rotated so that the same procedures and methods will function with a horizontal or any other orientation.

The preferred embodiment utilizes an accelerometer 29 mounted rigidly on the load beam assembly at the horizontal location 30 as prescribed by Equation (1) and FIG. 4, where the exact location is optimized by experiment as described above. The accelerometer orientation should be in a direction to measure vertical acceleration with positive sense either up or down. For the experimental work with the preferred embodiment wherein the ideas disclosed here were tested, the accelerometer was mounted to measure downward acceleration as positive.

Figure 5:
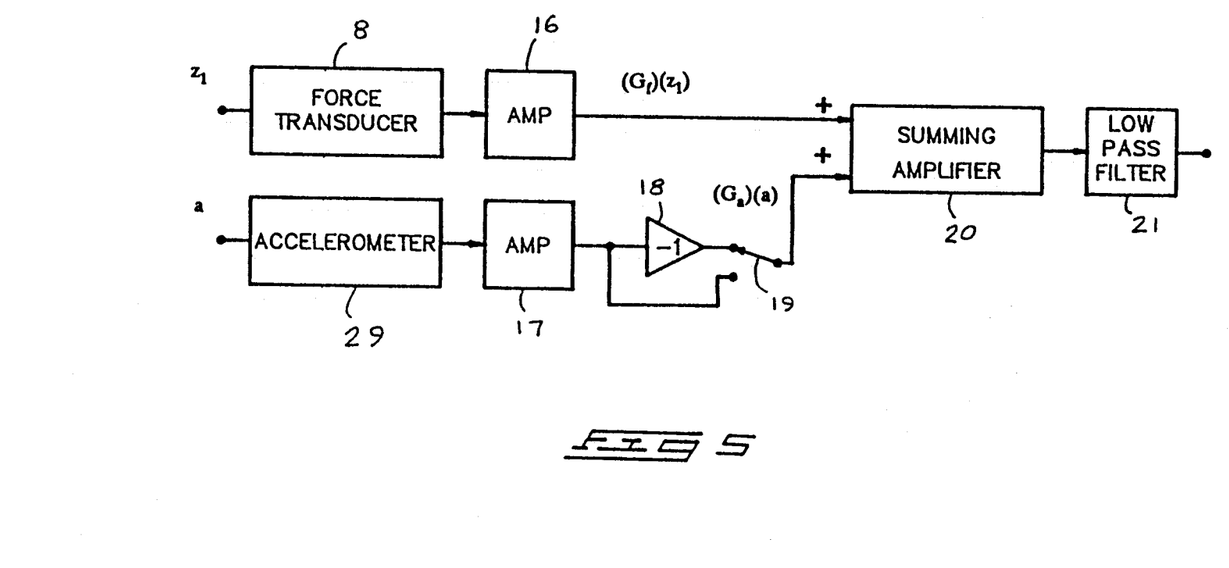
FIG. 5 is a schematic drawing for the compensation system.

FIG. 5 illustrates schematically the signal processing used to cancel the noise components of the first signal. The first signal is proportional to the force applied to the force transducer and hence is proportional to the spring compression $z_1$. The force transducer signal is amplified by an amplifier 16 such that the amplifier output, the first signal, is given by $(G_f)(z_1)$ where $G_f$ is a force transducer and amplifier gain factor relating spring compression $z_1$ to amplifier output $(G_f)(z_1)$.

In the preferred embodiment, the force transducer is a commercially available unit utilizing a bridge arrangement of strain gauge elements and is compensated for effects of temperature variation and for off-axis loading. Force transducer signal conditioning and amplifier details are well known and are not discussed further here. The gain factor $G_f$ is adjusted for proper calibration of the first signal so that it is an accurate measure of the load point force in the reference direction 25 when the acceleration inputs 26 and 27 are zero. The second signal is proportional to the vertical acceleration at the point on the load beam assembly where the accelerometer 29 is mounted. The accelerometer signal is amplified by an amplifier 17 such that the amplifier output, the second signal, is given by $(G_a)(a)$ where $G_a$ is an accelerometer and amplifier gain factor relating acceleration "a" to amplifier output $(G_a)(a)$.

In the preferred embodiment, the accelerometer is a commercially available unit utilizing a piezoelectric device located between a mounting base and a small mass. The accelerometer signal output is a charge proportional to acceleration and the amplifier is a charge amplifier whose input is charge and whose output is voltage. Methods of using accelerometers and charge amplifiers are well known. The gain $G_a$ and the position of the accelerometer are adjusted about the computed values so that the composite signal which is the sum $(G_f)(z_1) + (G_a)(a)$ of the first and second signals is as close as possible to zero for test combinations of acceleration inputs 26 and 27 and zero force 28 at the load point. This is an optimization process for which the criterion could be, for example, to minimize the average power in the composite signal, and the test combinations of acceleration inputs are similar to what would be observed during production. Any other means for measuring force and acceleration to result in the first and second signals, $(G_f)(z_1)$ and $(G_a)(a)$ as defined, could be used.

The inverter 18 and switch 19 shown in FIG. 5 allow the accelerometer to be mounted with positive acceleration defined in either the up or down direction, although as noted previously, the experimental work leading to this disclosure utilized down as the positive direction. The first and second signals are summed by a summing amplifier 20, to give a composite signal whose noise components have been removed.

For frequencies above some cutoff value, the model of FIG. 4 will no longer be valid; higher order modes can be excited for which the compensation system disclosed will not function adequately. These higher frequencies can be removed with low-pass filtering.

Before the signals are summed in the summing amplifier 20, no electronic filtering is used that would affect the signals in the measurement frequency range of interest. After summing occurs, a low-pass filter 21 can be employed, if desired, to remove frequency components above the measurement frequency range of interest.

This improvement has been specifically described with respect to its application to a simple beam having a force applied to the beam intermediate two spaced compliant supports. However, the load point need not always be located between the beam supports. It is to be understood that this system for compensation of errors is also applicable to other beam configurations, including cantilevered beams where the force might be applied at a location on the beam that is spaced outwardly from the beam supports. In this situation, the fraction L might be greater than one.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims appropriately interpreted in accordance with the doctrine of equivalents.

I claim:

1. A method of compensating for errors caused by accelerations of a load beam assembly interposed between a load point and first and second compliant supports located respectively at first and second reference points along the load beam assembly during measurement of a force applied to the load point on the load beam assembly along a reference direction, comprising the following steps:
   obtaining a first signal proportional to the compression of the first compliant support;
   obtaining a second signal proportional to acceleration along the reference direction of a selected location on the load beam assembly, the selected location being spaced from the first and second compliant supports on the load beam assembly, the acceleration of the selected location in the reference direction being directly proportional to the acceleration induced noise components of the first signal for any combination of acceleration inputs in the reference direction at the first and second compliant supports within a preselected frequency range; and
   adding the first signal to the second signal to obtain a composite signal that is proportional to the force in the reference direction at the load point and which is compensated for accelerations of the load beam assembly.

2. The method of claim 1, further including the following step: determining the position of the selected location on the load beam assembly as being on a line parallel to the reference direction and at a fraction L of the distance from a line through the second reference point to a line through the first reference point, wherein the lines through the first and second reference points are parallel to the reference direction and the fraction L is given by:

$$L = (1+R)/(R(1+h));$$

where:
   $R = Md^2/J$;
   M = mass of load beam assembly;
   d = distance from a line parallel to the reference direction and passing through the second reference point, to a line parallel to the reference direction and passing through the center of mass M;
   J = polar mass moment of the load beam assembly about an axis through the center of mass and perpendicular to the plane defined by the direction along the load beam assembly and the reference direction;
   $h = (d_2 - d)/d$; and
   $d_2$ = distance between lines parallel to the reference direction and passing through the first and second reference points.

3. The method of claim 1 wherein the constant of proportionality relating the first signal to compression of the first compliant support is a gain factor $G_f$ and the constant of proportionality relating the second signal to acceleration is a gain factor $G_a$ and wherein $G_f = ((K_1 d_2)/(Md))G_a$, where:
   $K_1$ = spring constant of the first compliant support;
   $d_2$ = distance between lines parallel to the reference direction and passing through the first and second reference points;
   M = mass of load beam assembly; and
   d = distance from a line parallel to the reference direction and passing through the second reference point, to a line parallel to the reference direction and passing through the center of mass M.

4. The method of claim 1, comprising the following additional step:
   determining the constant of proportionality relating acceleration to the second signal as the value that minimizes the composite signal average power in the absence of force applied at the load point for combinations of acceleration inputs at the compliant supports covering a frequency range for which the load beam assembly is accurately modeled as a rigid beam.

5. The method of claim 1, comprising the following additional step:
   removing frequency components of the composite signal above the preselected frequency range by low-pass filtering.

6. The method of claim 1, comprising the following additional step:
   determining the selected location for measuring acceleration on the load beam assembly as the location that minimizes the composite signal average power in the absence of force applied at the load point for combinations of acceleration inputs at the compliant supports covering a frequency range for which the load beam assembly is accurately modeled as a rigid beam.

7. Apparatus for compensating for errors caused by accelerations of a load beam assembly interposed between a load point and first and second compliant supports located respectively at first and second reference points along the load beam assembly during measurement of a force applied to the load point on the load beam assembly along a reference direction, comprising:

means for obtaining a first signal proportional to the compression of the first compliant support;

means for obtaining a second signal proportional to acceleration along the reference direction of a selected location on the load beam assembly, the selected location being spaced from the first and second compliant supports on the load beam assembly, the acceleration of the selected location in the reference direction being directly proportional to the acceleration induced noise components of the first signal for any combination of acceleration inputs in the reference direction at the first and second compliant supports within a preselected frequency range; and means for adding the first signal to the second signal to obtain a composite signal that is proportional to the force in the reference direction at the load point and which is compensated for accelerations of the load beam assembly.

8. The apparatus of claim 7 in which the selected location is on a line parallel to the reference direction, this line being located at a fraction L of the distance from a line through the second reference point to a line through the first reference point, the lines through the first and second reference points being parallel to the reference direction, the fraction L being given by:

$$L = (1+R)/(R(1+h));$$

where:

$R = Md^2/J$;

M = mass of load beam assembly;

d = distance from a line parallel to the reference direction and passing through the second reference point, to a line parallel to the reference direction and passing through the center of mass M;

J = polar mass moment of the load beam assembly about an axis through the center of mass and perpendicular to the plane defined by the direction along the load beam assembly and the reference direction;

h = $(d_2 - d)/d$; and $d_2$ = distance between lines parallel to the reference direction and passing through the first and second reference points.

9. The apparatus of claim 7 wherein the constant of proportionality relating the first signal to compression of the first compliant support is a gain factor $G_f$ and the constant of proportionality relating the second signal to acceleration is a gain factor $G_a$ and wherein $G_f = ((K_1 d_2)/(Md))G_{a2}$ where:

$K_1$ = spring constant of the first compliant support;

$d_2$ = distance between lines parallel to the reference direction and passing through the first and second reference points;

M = mass of load beam assembly; and d = distance from a line parallel to the reference direction and passing through the second reference point, to a line parallel to the reference direction and passing through the center of mass M.

10. The apparatus of claim 7, further comprising:

means for determining the constant of proportionality relating acceleration to the second signal as a computed optimum value that minimizes the composite signal average power in the absence of force applied at the load point for combinations of excitation inputs at the compliant supports covering a frequency range for which the load beam assembly is accurately modeled as a rigid beam.

11. The apparatus of claim 7, further comprising:

filter means for additionally removing high frequency components of the composite signal by low-pass filtering.

12. The apparatus of claim 7, further comprising:

means for determining the selected location for measuring acceleration on the load beam assembly as the location that minimizes the composite signal average power in the absence of force applied at the load point for combinations of acceleration inputs at the compliant supports covering a frequency range for which the load beam assembly is accurately modeled as a rigid beam.

13. Apparatus for compensating for errors caused by accelerations of a load beam assembly for measuring bending force of lumber applied through a load roller on the load beam assembly by a force applied to the load roller on the load beam assembly along a reference direction, comprising:

transducer means operably connected to one end of the load beam assembly for obtaining a first signal proportional to the force applied to the load roller on the load beam assembly by a piece of lumber being tested;

pivot means operably connected to the remaining end of the load beam;

accelerometer means mounted at a selected location on the load beam assembly for obtaining a second signal proportional to acceleration along the reference direction of the selected location on the load beam assembly, the selected location being spaced on the load beam assembly intermediate the transducer means and the pivot means, the acceleration of the selected location in the reference direction being directly proportional to the acceleration induced noise components of the first signal for any combination of acceleration inputs in the reference direction at the first and second compliant supports within a preselected frequency range; and means for adding the first signal to the second signal to obtain a composite signal that is proportional to the force in the reference direction at the load point and which is compensated for accelerations of the load beam assembly.

* * * * *

UNITED STATES PATENT AND TRADEMARK OFFICE
CERTIFICATE OF CORRECTION

PATENT NO. : 4,991,446
DATED : February 12, 1991
INVENTOR(S) : Friend K. Bechtel It is certified that error appears in the above-identified patent and that said Letters Patent is hereby corrected as shown below:

The presentation of equations (2) and (3) at column 7, lines 26-31 should be as follows:

$$Z_1(s) = -[(s^2+T_2(1+R))/D]A_1(s) - [T_2(hR-1)/D]A_2(s) \qquad (2)$$

$$A(s)/(T_1(1+h)) = [(s^2+T_2(1+R))/D]A_1(s) + [T_2(hR-1)/D]A_2(s) \qquad (3)$$

Signed and Sealed this

Seventh Day of July, 1992

Attest:

DOUGLAS B. COMER

Attesting Officer

Acting Commissioner of Patents and Trademarks